(12) United States Patent
Novakovic et al.

(10) Patent No.: US 8,545,554 B2
(45) Date of Patent: Oct. 1, 2013

(54) INTRAOCULAR INJECTOR

(75) Inventors: Zoran Novakovic, Irvine, CA (US); Rahul Bhagat, Irvine, CA (US); Shawn R. Davis, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 115 days.

(21) Appl. No.: 12/355,709

(22) Filed: Jan. 16, 2009

(65) Prior Publication Data
US 2010/0185205 A1 Jul. 22, 2010

(51) Int. Cl.
*A61F 2/16* (2006.01)
*A61F 9/007* (2006.01)

(52) U.S. Cl.
USPC .......................................... 623/6.12; 606/107

(58) Field of Classification Search
USPC .................. 606/107; 623/1.12, 6.12, 6.11
See application file for complete search history.

(56) References Cited

U.S. PATENT DOCUMENTS

| | | |
|---|---|---|
| 2,513,014 A | 6/1950 | Fields |
| 2,717,599 A | 9/1955 | Huber |
| 3,220,413 A | 11/1965 | Sunnen |
| 3,238,941 A | 3/1966 | Klein et al. |
| 3,698,390 A | 10/1972 | Ferris |
| 3,937,370 A | 2/1976 | Witty |
| 3,941,128 A | 3/1976 | Baldwin |
| 4,105,030 A | 8/1978 | Kercso |
| 4,144,317 A | 3/1979 | Higuchi et al. |
| 4,304,765 A | 12/1981 | Shell et al. |
| 4,383,992 A | 5/1983 | Lipari |
| 4,521,210 A | 6/1985 | Wong |
| 4,597,753 A | 7/1986 | Turley |
| 4,668,506 A | 5/1987 | Bawa |
| 4,727,064 A | 2/1988 | Pitha |
| 4,799,478 A | 1/1989 | Fedorov et al. |
| 4,803,075 A | 2/1989 | Wallace et al. |
| 4,834,094 A * | 5/1989 | Patton et al. .................. 606/107 |

(Continued)

FOREIGN PATENT DOCUMENTS

| | | |
|---|---|---|
| EP | 0197718 | 10/1986 |
| EP | 0270 247 | 6/1988 |

(Continued)

OTHER PUBLICATIONS

Aukunuru et al., "In Vitro Delivery of Nano- and Micro-Particles to Human Retinal Pigment Epthelial (ARPE-19) Cells", Drug Delivery Technology, vol. 2, No. 2, Mar./Apr. 2002, pp. 50-57.

(Continued)

*Primary Examiner* — Ryan Severson
*Assistant Examiner* — Anh Dang
(74) *Attorney, Agent, or Firm* — Laura L. Wine; Joel B. German; Debra D. Condino

(57) ABSTRACT

An intraocular injector includes a syringe body having open-ended cone disposed in one end thereof along with a piston disposed in the body. A transparent implant holder having a lumen therein is aligned with an open-ended cone, a needle include a proximal end and a distal end with a bevel disposed on the distal end of the needle. A plunger affixed to the piston and slidable within a holder lumen and needle lumen is provided for injecting solid intraocular implants into an eye. A cylindrical syringe body shape facilitates control over the needle bevel orientation during injection of the implant into the eye.

6 Claims, 3 Drawing Sheets

(56) References Cited

U.S. PATENT DOCUMENTS

| | | | |
|---|---|---|---|
| 4,846,809 A | 7/1989 | Sims | |
| 4,850,970 A | 7/1989 | Sutherland | |
| 4,852,566 A * | 8/1989 | Callahan et al. | 606/107 |
| 4,853,224 A | 8/1989 | Wong | |
| 4,900,304 A | 2/1990 | Fujioka et al. | |
| 4,907,587 A | 3/1990 | Fedorov et al. | |
| 4,915,686 A | 4/1990 | Frederick | |
| 4,920,104 A | 4/1990 | DeVore et al. | |
| 4,941,874 A | 7/1990 | Sandow et al. | |
| 4,959,217 A | 9/1990 | Sanders et al. | |
| 4,997,652 A | 3/1991 | Wong | |
| 5,014,717 A | 5/1991 | Lohrmann | |
| 5,059,172 A | 10/1991 | Sutherland et al. | |
| 5,098,443 A | 3/1992 | Parel et al. | |
| 5,164,188 A | 11/1992 | Wong | |
| 5,188,607 A | 2/1993 | Wu | |
| 5,219,339 A | 6/1993 | Saito | |
| 5,250,026 A | 10/1993 | Ehrlich et al. | |
| 5,256,408 A | 10/1993 | Babcock et al. | |
| 5,279,554 A | 1/1994 | Turley | |
| 5,284,479 A | 2/1994 | DeJong | |
| 5,324,718 A | 6/1994 | Loftsson | |
| 5,332,582 A | 7/1994 | Babcock et al. | |
| 5,336,206 A | 8/1994 | Shichman | |
| 5,354,333 A * | 10/1994 | Kammann et al. | 623/6.12 |
| 5,378,475 A | 1/1995 | Smith et al. | |
| 5,443,505 A | 8/1995 | Wong et al. | |
| 5,451,213 A | 9/1995 | Teicher et al. | |
| 5,466,233 A | 11/1995 | Weiner et al. | |
| 5,476,511 A | 12/1995 | Gwon et al. | |
| 5,494,901 A | 2/1996 | Javitt et al. | |
| 5,501,856 A | 3/1996 | Ohtori et al. | |
| 5,516,522 A | 5/1996 | Peyman et al. | |
| 5,576,311 A | 11/1996 | Guy | |
| 5,582,591 A | 12/1996 | Cheikh | |
| 5,616,123 A | 4/1997 | Cheikh | |
| 5,620,450 A * | 4/1997 | Eagles et al. | 606/107 |
| 5,651,774 A | 7/1997 | Taranto et al. | |
| 5,656,026 A | 8/1997 | Joseph | |
| 5,725,521 A | 3/1998 | Mueller | |
| 5,746,718 A | 5/1998 | Steyn | |
| 5,766,242 A | 6/1998 | Wong et al. | |
| 5,770,589 A | 6/1998 | Billson et al. | |
| 5,807,400 A | 9/1998 | Chambers et al. | |
| 5,817,075 A | 10/1998 | Giungo | |
| 5,824,001 A | 10/1998 | Erskine | |
| 5,824,072 A | 10/1998 | Wong | |
| 5,869,079 A | 2/1999 | Wong et al. | |
| 5,876,373 A | 3/1999 | Giba et al. | |
| 5,941,250 A | 8/1999 | Aramant et al. | |
| 5,957,892 A | 9/1999 | Thorne | |
| 6,074,661 A | 6/2000 | Olejnik et al. | |
| 6,107,347 A | 8/2000 | Francese et al. | |
| 6,117,443 A | 9/2000 | Cherif-Cheikh | |
| 6,120,786 A | 9/2000 | Cherif Cheikh | |
| 6,142,972 A | 11/2000 | Cheikh | |
| 6,159,218 A | 12/2000 | Aramant et al. | |
| 6,190,350 B1 | 2/2001 | Davis et al. | |
| 6,217,895 B1 | 4/2001 | Guo et al. | |
| 6,251,418 B1 | 6/2001 | Ahern et al. | |
| 6,271,216 B1 | 8/2001 | Mello et al. | |
| 6,331,313 B1 | 12/2001 | Wong et al. | |
| 6,395,294 B1 | 5/2002 | Peyman | |
| 6,407,079 B1 | 6/2002 | Muller et al. | |
| 6,450,937 B1 | 9/2002 | Mercereau et al. | |
| 6,548,078 B2 | 4/2003 | Guo et al. | |
| 6,554,760 B2 | 4/2003 | Lamoureux et al. | |
| 6,605,093 B1 * | 8/2003 | Blake | 606/107 |
| 6,639,116 B2 | 10/2003 | Lever et al. | |
| 6,648,857 B1 | 11/2003 | Pedigo | |
| 6,699,493 B2 | 3/2004 | Wong | |
| 6,713,081 B2 | 3/2004 | Robinson et al. | |
| 6,719,750 B2 | 4/2004 | Varner et al. | |
| 6,723,353 B2 | 4/2004 | Beck et al. | |
| 6,899,717 B2 | 5/2005 | Weber et al. | |
| 7,189,245 B2 | 3/2007 | Kaplan | |
| 7,651,505 B2 | 1/2010 | Lubock et al. | |
| 2002/0026176 A1 | 2/2002 | Varner et al. | |
| 2002/0082609 A1 | 6/2002 | Green | |
| 2002/0198174 A1 | 12/2002 | Lyons | |
| 2003/0060763 A1 | 3/2003 | Penfold et al. | |
| 2003/0171320 A1 | 9/2003 | Guyer | |
| 2003/0208218 A1 | 11/2003 | Kadziauskas et al. | |
| 2004/0024412 A1 * | 2/2004 | Clements et al. | 606/107 |
| 2004/0054374 A1 | 3/2004 | Weber et al. | |
| 2004/0057979 A1 | 3/2004 | Wong et al. | |
| 2004/0077562 A1 | 4/2004 | Chandavarkar et al. | |
| 2004/0152664 A1 | 8/2004 | Chang et al. | |
| 2004/0170665 A1 | 9/2004 | Donovan | |
| 2005/0032747 A1 | 2/2005 | Bartolini et al. | |
| 2005/0049605 A1 * | 3/2005 | Vaquero et al. | 606/107 |
| 2005/0154399 A1 * | 7/2005 | Weber et al. | 606/107 |
| 2006/0108012 A1 | 5/2006 | Barrow | |
| 2006/0173060 A1 | 8/2006 | Chang et al. | |
| 2008/0097459 A1 | 4/2008 | Kammerlander | |
| 2008/0200921 A1 * | 8/2008 | Downer | 606/107 |

FOREIGN PATENT DOCUMENTS

| | | |
|---|---|---|
| EP | 0270257 | 6/1988 |
| EP | 0304700 | 8/1988 |
| EP | 0415504 | 3/1991 |
| EP | 0544948 | 9/1995 |
| EP | 1419748 | 11/2002 |
| EP | 1323450 | 7/2003 |
| EP | 1 323 450 | 9/2004 |
| WO | WO 91/12048 | 8/1991 |
| WO | WO 99/33512 | 7/1999 |
| WO | WO 99/53991 | 10/1999 |
| WO | WO 00/02564 | 1/2000 |
| WO | WO 02/089815 | 11/2002 |
| WO | WO 2004/026106 | 4/2004 |
| WO | WO 2004/069280 | 8/2004 |
| WO | WO 2004/087043 | 10/2004 |
| WO | WO 2005/055873 | 6/2005 |
| WO | WO 2006/071554 | 7/2006 |

OTHER PUBLICATIONS

Beer et al., "Intraocular Concentration and Pharmacokinetics of Triamcinolone Acetonide After a Single Intravitreal Injection", Ophthalmology, vol. 110, No. 4, Apr. 2003, pp. 681-686.

Cheng et al., "Intravitreal Sustained-Release Dexamethasone Device in the Treatment of Experimental Uveitis", Investigatative Ophthalmology & Visual Science, Feb. 1995, vol. 36, No. 2, pp. 442-453.

Crabb et al., "Cloning of the cDNAs encoding the cellular retinaldehyde-binding protein from bovine and human retina and comparison of the protein structures", J. Biol. Chem., 265(35), 1988, pp. 18688-18692.

Dunn et al., ARPE-19, a human retinal pigment epithelial cell line with differentiated properties, Exp. Eye Res 62 (1996), pp. 155-169.

Enyedi et al., "An Intravitreal Device Providing Sustained Release of Cyclosporine and Dexamethasone", Current Eye Research (1995) pp. 549-557.

Klimanskaya et al., "Derivation and comparative assessment of retinal pigment epithelium from human embryonic stem cells using transcriptomics", Cloning and Stem Cells 6(3), 2004, 99. 217-245.

Kochinke et al., "Biodegradable Drug Delivery System for Uveitis Treatment", Investigative Ophthalmology & Visual Science, Feb. 15, 1996, vol. 37, No. 3, 186-B98.

Rao et al., "Preparation and Evaluation of Ocular Inserts Containing Norfloxacin", Turk. J. Med. Sci. (2004) 34, pp. 239-246.

Rogojina et al., "Comparing the use of affymetrix to spotted oligonucleotide microarrays using two retinal pigment epithelium cell lines", Molecular Vision, 9, 2003, pp. 482-496.

Streilein et al., "Ocular Immune Privilege: Therapeutic Opportunities from an Experiment of Nature", Nature Review Immunology (2003), 3, pp. 879-889.

USP 23; NF 18 (1995) pp. 1790-1798.

Yeung et al., "Cytotoxicity of Triamcinolone on Cultured Human Retinal Pigment Epithelial Cells: Comparison with Dexamethasone and Hydrocortisone", Jpn. J. Ophthal., 48 (2004), pp. 236-242.

* cited by examiner

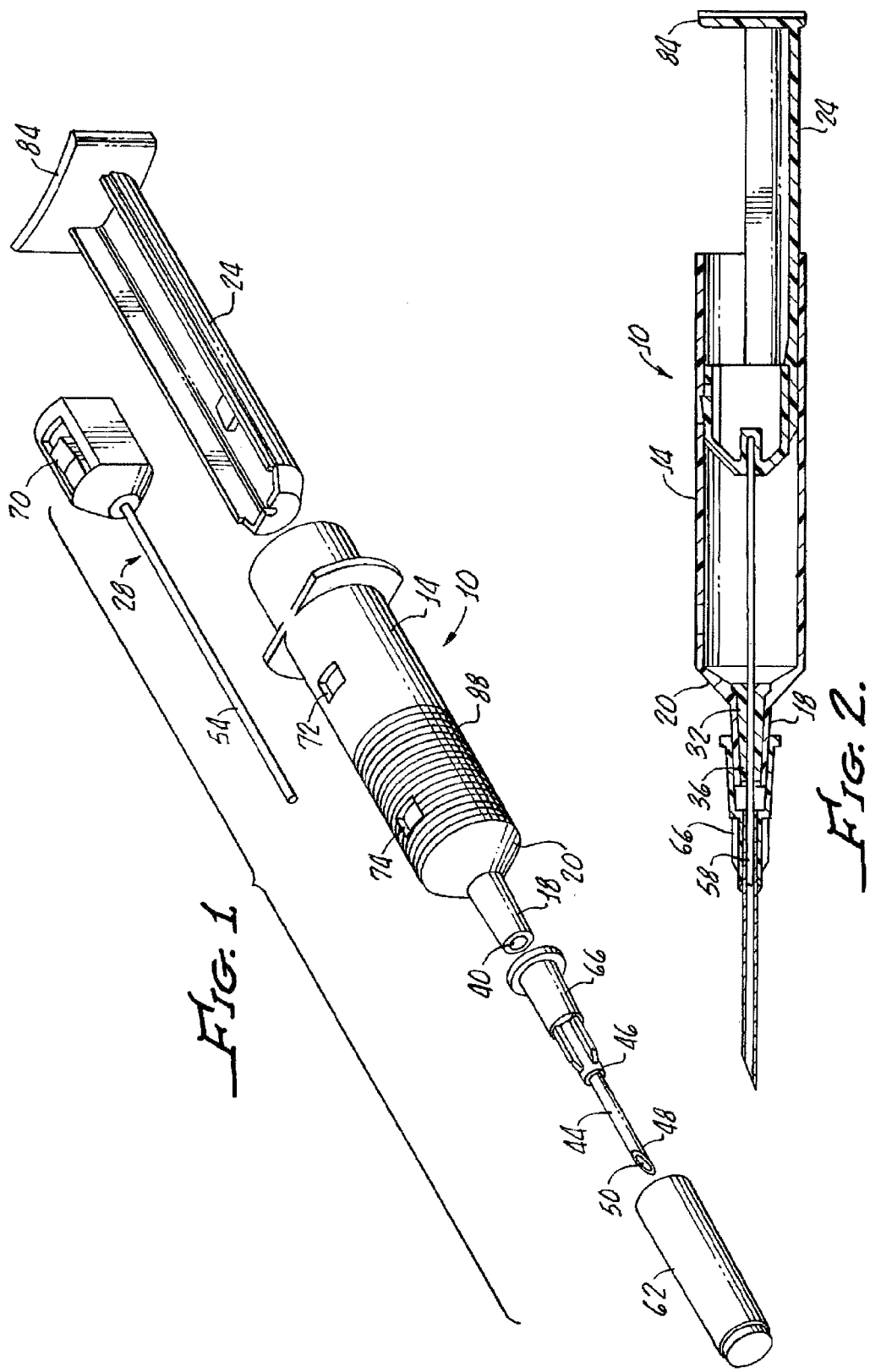

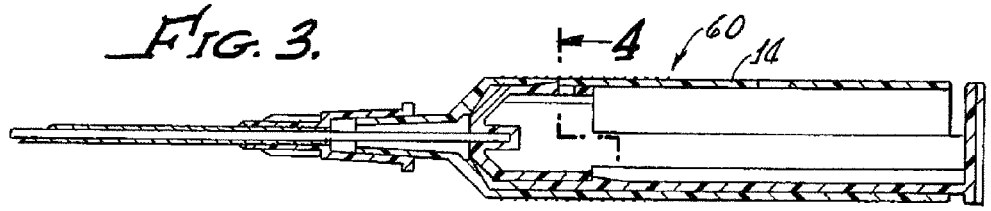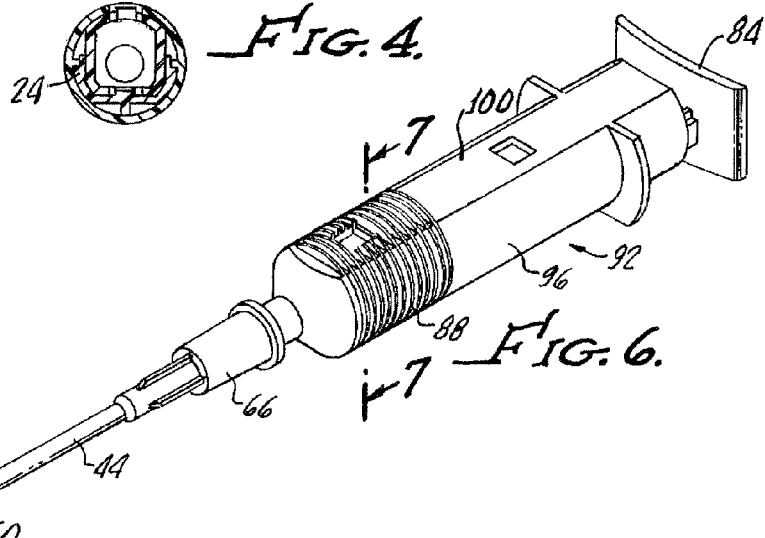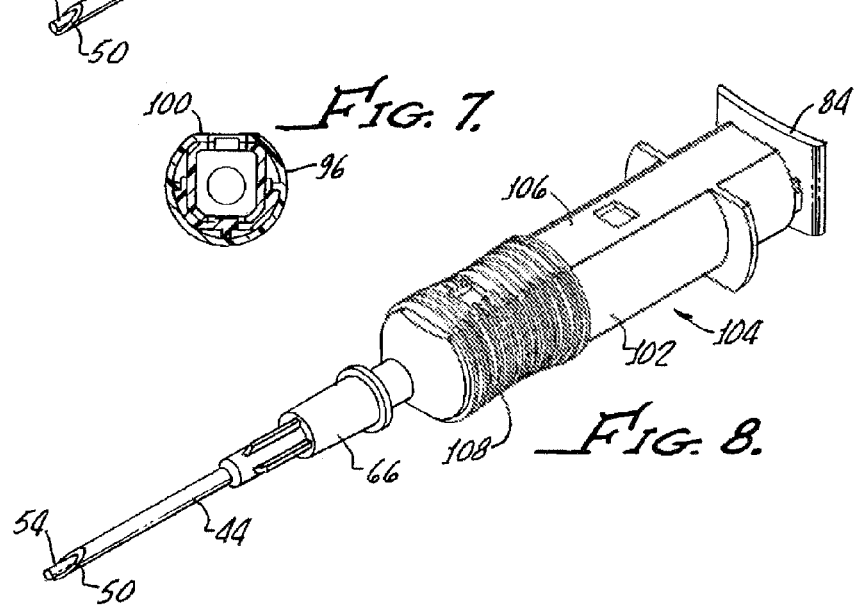

INTRAOCULAR INJECTOR

The present invention relates to apparatus and methods for implanting ocular implants in eyes. More particularly, the invention relates to such apparatus and methods for implanting, for example, delivering, placing, positioning and the like, particulate ocular implants in an eye, for example, at one or more of various locations in an eye, for example, a mammalian eye.

The mammalian eye is a complex organ comprising an outer covering including the sclera (the tough white portion of the exterior of the eye) and the cornea (the clear outer portion covering the pupil and iris). In a medial cross section, from anterior to posterior, the eye comprises features including, without limitation: the cornea, the anterior chamber (a hollow feature filled with a watery, clear fluid called the aqueous humor and bounded by the cornea in the front and the lens in the posterior direction), the iris (a curtain-like feature that can open and close in response to ambient light), the lens, the posterior chamber (filled with a viscous fluid called the vitreous humor), the retina (the innermost coating of the back of the eye and comprising light-sensitive neurons), the choroid (an intermediate layer providing blood vessels to the cells of the eye), and the sclera. The posterior chamber comprises approximately ⅔ of the inner volume of the eye, while the anterior chamber and its associated features (lens, iris etc.) comprise about ⅓ of the eye's inner volume.

Ocular implants containing one or more therapeutic components combined with matrix components, such as polymeric components, have been proposed for use, for example, to treat conditions/diseases of the eye. Such implants have been suggested for use at various locations in the eye, for example, in the vitreous, subconjunctivally, anterior chamber and posterior chamber of the eye.

It is important that accurate placement of the implant is effected. This requires accurate manipulation of an implant needle including orientation of the needle during entry of the needle and injection of the implant.

Thus, there continues to be a need for apparatus and methods to effect dry implant microparticles in an eye.

SUMMARY OF THE INVENTION

An intraocular injector in accordance with the present invention includes a syringe body having an open-ended cone disposed on one end thereof. A piston is disposed within the body and a transparent implant holder having a lumen therein, which is aligned with the open-end of the cone, provides sufficient transparency to enable visual observation of the solid intraocular implants disposed within the lumen holder.

A needle is provided having a proximal end, a distal end, and a lumen extending therethrough. The proximal end of the needle is supported by a transparent needle hub which is attachable to the cone with a needle lumen aligned with the implant holder lumen.

A plunger, affixed to the piston and slidable within the holder lumen and needle lumen, is provided for injecting solid intraocular implants into an ocular site.

A bevel is disposed in a distal end of the needle and a cylindrical syringe body shape facilitates controls needle bevel orientation during the injection of the implant into the eye. This feature coupled with the transparency of the implant holder and needle hub enable accurate control and placement of the implant.

To further facilitate control of the needle bevel orientation circumferential ribs are provided on the syringe body. The circumferential ribs may have an hourglass profile in longitudinal cross section and this shape is particularly useful in controlling longitudinal (push-pull) movement of the syringe body and the needle placement at an ocular site.

Alternatively, the cylindrical body may include a longitudinal flat thereon which may, if desired, be aligned with the bevel to facilitate orientation thereof during implant procedures.

One embodiment of the present invention of the injector includes an implant holder which is totally enclosed by the needle hub. In another embodiment, the implant holder may be partially enclosed by the needle hub and partially enclosed by the syringe body cone. In yet another embodiment of the present invention, an implant holder may be totally enclosed by the syringe body cone. All of these elements being transparent in order to accurately determine by visual observation and placement of implants within the intraocular injector prior to injecting the implants into an ocular region or site.

Methods for implanting an ocular implant in an ocular site are also provided. More specifically, the methods include providing an intraocular injector comprising a cylindrical syringe body with a plunger and piston disposed therein and a needle attached to the syringe body. The needle includes a distal end with a bevel thereon.

The method further includes placing a needle distal end proximate the ocular site and orienting the bevel by way of turning the cylindrical body to the desired bevel orientation. The cylindrical nature of the body facilitates turning an operation of the plunger despite orientation of the needle.

The method further includes inserting a needle distal end into the ocular site in a desired depth and operating the plunger piston to force the implants through the needle lumen into the ocular site.

The method in accordance with the present invention further includes providing an intraocular injector with a flatted cylindrical syringe body with a plunger piston disposed therein and a needle attachable to the syringe body having a distal end with a bevel thereon.

The method further includes attaching a needle to the syringe using a needle hub with the needle bevel aligned with the cylindrical body flat and placing a needle piston end proximate in an ocular site and thereafter orienting the bevel by way of turning the cylindrical body as indicated by the flap.

The present apparatus and methods can be practiced to treat a condition of the posterior segment of a mammalian eye, such as a condition selected from the group consisting of macular edema, dry and wet macular degeneration, choroidal neovascularization, diabetic retinopathy, acute macular neuroretinopathy, central serous chorioretinopathy, cystoid macular edema, and diabetic macular edema, uveitis, retinitis, choroiditis, acute multifocal placoid pigment epitheliopathy, Behcet's disease, birdshot retinochoroidopathy, syphilis, lyme, tuberculosis, toxoplasmosis, intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; retinal arterial occlusive disease, anterior uveitis, retinal vein occlusion, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemiretinal vein occlusion, papillophlebitis, central retinal artery occlusion, branch retinal artery occlusion, carotid artery disease (CAD), frosted branch angiitis, sickle cell retinopathy, angioid streaks, familial exudative vitreoretinopathy, and Eales disease; traumatic/surgical conditions such as sympathetic ophthalmia, uveitic retinal disease, retinal detachment, trauma, photocoagulation, hypoperfusion during surgery, radiation retinopathy, and bone marrow transplant retinopathy; proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; punctate inner choroidopathy, acute posterior multifocal placoid pigment epitheliopathy, myopic retinal degeneration, acute retinal pigment epithelitis, retinitis pigmentosa, proliferative vitreal retinopathy (PVR), age-related macular degeneration (ARMD), diabetic retinopathy, diabetic macular edema, retinal detachment, retinal tear, uveitis, cytomegalovirus retinitis and glaucoma comprises administering to the posterior segment of the eye a composition comprising an SIRT1-activating agent in an ophthalmically effective vehicle. Conditions treated with the present apparatus and methods may be intraocular conditions involving ocular degeneration, such as neurodegeneration of retinal ganglion cells.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings.

BRIEF DESCRIPTION OF THE DRAWINGS

FIG. 1 is an exploded perspective view of an intraocular injector in accordance with the present invention generally shown a cylindrical syringe body, a piston disposed within the body along with a transparent implant holder, a needle with a bevel thereon, and a plunger slidable affixed to the piston for injecting a solid intraocular implants (not shown) through a holder lumen a needle lumen;

FIG. 2 is a cross sectional view of the injector shown in FIG. 1 with the plunger piston shown in a first position (not an initial position) before injection of solid ophthalmic implant;

FIG. 3 is a cross sectional view similar to FIG. 2 showing the piston plunger moved to a second position thereby injecting solid intraocular implants into an eye (not shown) through the holder lumen and needle lumen;

FIG. 4 is a cross sectional view taken along the line 4-4 of FIG. 3 illustrating the cylindrical shape of the syringe body;

FIG. 6 is an alternative embodiment of the present invention illustrating an injector having a cylindrical body with a flat thereon;

FIG. 7 is a cross sectional view taken along the line 6-6 of FIG. 5 illustrating the flatted syringe body;

FIG. 8 is a further perspective view of an injector in accordance with the present invention illustrating ribs on the cylindrical body which have an hourglass profile in longitudinal cross section;

DETAILED DESCRIPTION

Figure 5:
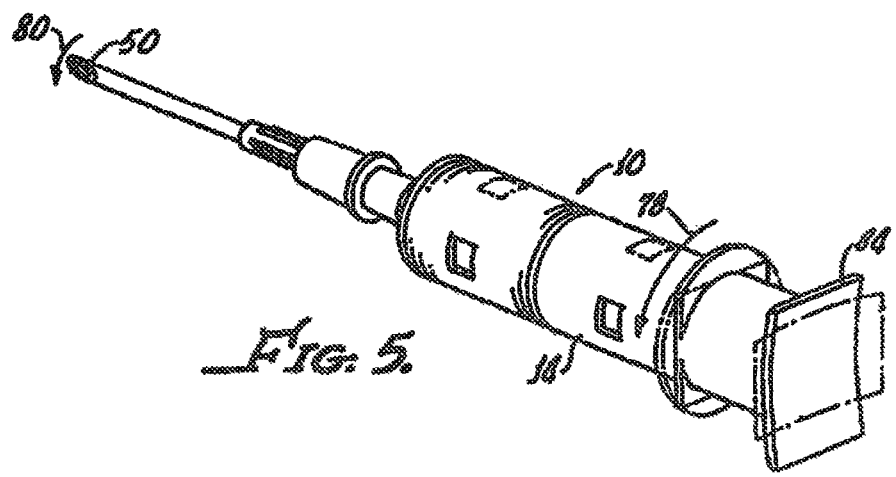
FIG. 5 is a perspective view of an injector in accordance with the present invention and illustrating the function of the cylindrical body in orienting the bevel needle and method for implanting an ocular implanting to an eye in accordance with the present invention.

As described herein, administration of a therapeutic agent through the use of one or more intraocular implants may improve treatment of undesirable ocular conditions. Definitions For the purposes of this description, we use the following terms as defined in this section, unless the context of the word indicates a different meaning.

As used herein, an "intraocular implant" refers to a device or element that is structured, sized, or otherwise configured to be placed in an eye. Intraocular implants may be permanent or biocompatible with physiological conditions of an eye and do not cause adverse side effects. Intraocular implants may be placed in an eye without disrupting vision of the eye.

As used herein, a "therapeutic component" refers to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases;, corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "substantially transparent" as used herein refers to a transparency which allows an observer of the holder or needle hub held at arms length to determine that an implant is present in the holder before injection without use by the observer of magnification aid or other than normal ambient or indoor lighting.

The term "treat", "treating", or "treatment" as used herein, refers to reduction or resolution or prevention of an ocular condition, ocular injury or damage, or to promote healing of injured or damaged ocular tissue.

With reference to FIGS. 1-3, there is shown a disposable hand held intraocular injector 10 in accordance with the present invention which generally includes a syringe body 14 formed, from a transparent thermoplastic such as a polycarbonate, or acrylic, the holder 32 includes a lumen 36 aligned with an open-end 40 of the cone 18.

The Intraocular injector 10 is useful for administering a drug delivery system ("DDS"). The DDS can be a solid implant containing a therapeutic agent or agent such as Brimonidine Tartrate homogenously distributed throughout a biodegradable (i.e. PLGA) polymer matrix. The injector can be used to administer the implant into the vitreous (posterior chamber) or anterior humor (anterior chamber) or subconjunctival (i.e. into the sub-tenon space, that is within the cornea) of a human eye. The resulting sustained (multi-week) release of the brimonidine acts to treat glaucoma by lowering intraocular pressure and/or providing neuroprotection to the optic nerve at the retina. The invention is the injector for the DDS, not the DDS itself.

A body 14 includes an open-ended cone 18 on one end 20 of the body 14. A piston 24 is slidably disposed within the body 14 and carries a plunger 28 slidably affixed thereto. A transparent implant holder 32, formed from any suitable material, such as for example, a thermal plastic elastomer (TPE) thermoplastic rubber (TPR) or Silicone, which is a class of copolymers or a physical mix of polymers which consists of materials with both thermal plastic and elastomeric properties and are injected molded to provide ergometric handing thereof. The holder 32 includes a lumen 36 aligned with an open-end 40 of the cone 18. The holder 32, as well as other components of the injector in accordance with the present invention, all have sufficient transparency to enable visual observation of solid intraocular implants (not shown) disposed within the lumen holder 32 prior to injection into an ocular site (not shown).

Injection is made through a needle, or cannula, 44 which has a proximal end 46 and a distal end 48 with the distal end 48 including a bevel 50. The bevel 50 facilitates entry of the needle 44 into eye tissue and further facilitates placement of the intraocular implants into the ocular site. While a single bevel 50 is shown for illustrative purposes, a multifaceted bevel, not shown, may be utilized.

The needle 44 is suitable for delivering a 6 mm×0.37 mm solid implant to (within) a human eye; such as 22 gauge or smaller injector sharp needle 44 bore; siliconized, low cornea penetration force injector needle 44. The needle 44 may be about 5 mm to about 13 mm long. The injector 10 can be gamma radiation sterilized without loss of any functionality.

The plunger 28 includes a rod 54 which is slidable within the holder lumen 36 and a needle lumen 58, see FIG. 2, for injecting solid intraocular implants (not shown) into an ocular site (not shown). A syringe cap, or sheath, 62 is removably attachable to a transparent needle hub 66 for preventing accidental exposure of the needle 44. The hub 66 supports the needle proximal end 46 and is attachable to the cone 18 with the needle lumen 58 aligned with the implant holder lumen 36.

The plunger 28 may include a tab 70 which is depressible for engaging opening 72, for locking the plunger 28 within the body 14 before use. Upon release of the tab 70, by depression, the plunger 70 may be moved in a forward position until engagement with the opening 74 upon completion of a implant procedure, as illustrated in FIG. 3. An audible clicking sound signals the end of the injection and the locked plunger eliminates exposure of the distal end 48 upon removal of the needle 44 from the eye.

FIG. 4 is a cross section of the injector illustrating more clearly the cylindrical shape of the body which is important for facilitating control over the needle bevel 50 during injection of the implant into the ocular site as illustrated in FIG. 5.

As illustrated, turning of the syringe body 14 as indicated by the arrow 78, turns the needle bevel 50, as indicated by the arrow 80. At any rotational, position of the barrel enables easy manipulation of a piston thumb pad 84. Consistent gripping surface on the body 14 is provided by a cylindrical configuration. This must be contrasted with many prior art injectors (not shown) utilizing non-cylindrical syringe bodies.

To further facilitate the handling of the syringe during such orientation, circumferential ribs 88 may be provided on a syringe body 14.

Needle bevel 50 orientation may be further aided by another embodiment 92 shown in FIGS. 6-8 in which a syringe body 96 includes a flat 100 and which can be aligned with the needle bevel 50.

All of the components of the embodiment 92 which are identical or substantially similar to the injector 10 hereinabove described are identified by identical character references.

Yet further embodiment 104 shown in FIG. 8 includes a syringe body 102 having a flat 106 thereon, also aligned with the bevel 50 of the needle 44 yet including circumferential ribs 108 which have an hourglass profile, along a longitudinal cross section, to provide a more ergonomic grasping surface for a user.

Figure 9:
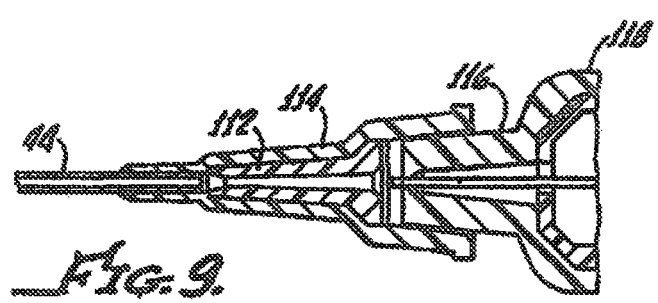
FIG. 9 is an enlarged cross sectional view of the syringe body cone transparent implant holder, needle hub, and needle illustrating one embodiment in accordance with the present invention in which the implant holder is totally enclosed by the needle hub.
Figure 10:
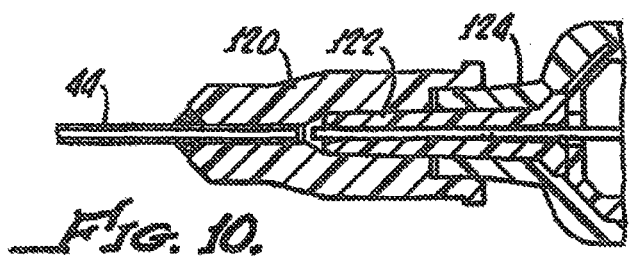
FIG. 10 is an enlarged cross sectional view of another embodiment in accordance with the present invention wherein the implant holder is partially enclosed by the needle hub and partially enclosed by the syringe body cone.
Figure 11:
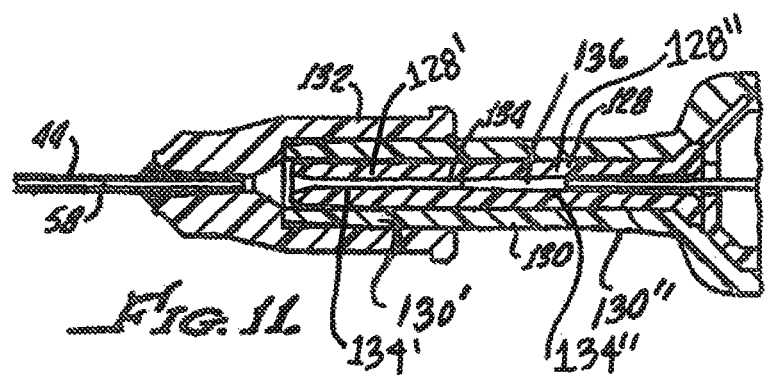
FIG. 11 is a further embodiment of the present invention shown in cross section wherein the implant holder is totally enclosed by the syringe body cone.

Various implant hub, needle hub, and syringe body cone configurations are shown in FIGS. 9-11. FIG. 9 illustrates implant holder 112 disposed and totally enclosed by a needle hub 114 when the needle hub 114 is disposed onto a syringe cone 116. This enables all of the implants disposed within the implant holder 112 to be attachable to any corresponding syringe body 118.

In addition, the visibility of the implant is improved since only two layers of clear plastic, the implant holder 112 and needle hub 114 cover the implant. In addition, the cone 116 and syringe body may be made form any material, not just a clear material.

Alternatively, as shown in FIG. 10, an implant holder 122 may be partially enclosed by a needle hub 120 and partially enclosed by a syringe cone 124. This may further facilitate alignment of the components.

Illustrated in FIG. 11, an implant holder 128 may be totally enclosed by the cone 130. As shown, the needle hub 132 is secured to a distal end of the cone 130 such that the needle hub 132 covers a portion, or distal section 130', of the cone 130, leaving a proximal portion 130" of the cone uncovered by the needle hub 132. As illustrated, the needle hub 132 also covers a distal section 128', of the implant holder 128, leaving a proximal section 128" of the implant holder 128 uncovered by the needle hub 132. As illustrated, the needle hub 132 also covers a distal section 134', of the implant holder lumen 134, leaving a proximal section 134" of the implant holder lumen 134 uncovered by the needle hub 132. This configuration provides easier verification of implant presence in the implant holder lumen 134 if the implant 136 is positioned outside of the distal section of the cone 130', covered by the needle hub 132.

EXAMPLE

A needle and a hub holder contain implants is attached to a syringe body as shown in FIG. 5. Thereafter, the needle bevel is oriented, by turning of the syringe body by gripping the circumferential ribs, to a desired position and thereafter injecting an implant from the needle by moving the piston and plunger by the pressing the thumb pad. Movement of the implant through the needle hub and implant holder is observed during the procedure resulting in definite placement of the implant in an ocular site.

Although there has been hereinabove described a specific syringe device for intraocular use in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. An intraocular injector comprising:
a syringe comprising a substantially cylindrical body, and an open ended cone disposed on a distal end of the body and being narrower than the body;
a piston disposed within said body;
a substantially transparent implant holder disposed entirely within the open ended cone, the substantially transparent implant holder having a lumen therein, and a solid intraocular implant disposed in the lumen;
a needle having a proximal end, a distal end, and a lumen extending therethrough, wherein the needle is spaced apart from the substantially transparent implant holder;
a substantially transparent needle hub supporting the needle proximal end and covering a distal portion of the open ended cone and a distal portion of the substantially transparent implant holder inside the open ended cone, leaving a proximal portion of the open ended cone and a proximal portion of the substantially transparent implant holder uncovered by the substantially transparent needle hub;
the solid ocular implant being located in the lumen of the substantially transparent implant holder in the uncovered proximal portion of the substantially transparent implant holder at a position outside of the open ended cone portion covered by the substantially transparent needle hub;
a plunger fixed to said piston and slidable within the substantially transparent implant holder lumen and needle lumen for injecting the solid intraocular implant into an eye; and
a bevel disposed on the distal end of said needle.

2. The injector according to claim 1, further comprising a gripping feature disposed on the body.

3. The injector according to claim 2, wherein the gripping feature comprises circumferential ribs.

4. The injector according to claim 1, wherein the body includes a longitudinal flat thereon.

5. The intraocular injector according to claim 4, wherein the injector further comprises circumferential ribs disposed on the longitudinal flat.

6. An intraocular injector comprising:
- a syringe comprising a substantially cylindrical body including a flattened portion and a shoulder, and an open ended cone disposed distally of the shoulder and being narrower than the body;
- a piston disposed within said body;
- an implant holder disposed entirely within the open ended cone, the implant holder having a lumen therein;
- a needle having a proximal end, a distal end, and a lumen extending therethrough, wherein the needle is spaced apart from the implant holder;
- a needle hub supporting the needle proximal end and covering a distal portion of the open ended cone and a distal portion of the implant holder inside the open ended cone, leaving a proximal portion of the open ended cone and a proximal portion of the implant holder uncovered by the needle hub;
- a plunger fixed to said piston and slidable within the implant holder lumen and needle lumen for injecting a solid intraocular implant into an eye; and
- a bevel disposed on the distal end of said needle and aligned with the flattened portion of the body.

* * * * *